United States Patent
Sun et al.

(10) Patent No.: US 11,433,559 B2
(45) Date of Patent: Sep. 6, 2022

(54) MAGNETICALLY CONTROLLABLE ROBOTIC DEVICE AND ITS METHOD OF MAKING

(71) Applicant: City University of Hong Kong, Kowloon (HK)

(72) Inventors: Dong Sun, Kowloon (HK); Pan Liao, Kowloon (HK); Liuxi Xing, Kowloon (HK)

(73) Assignee: City University of Hong Kong, Kowloon (HK)

( * ) Notice: Subject to any disclaimer, the term of this patent is extended or adjusted under 35 U.S.C. 154(b) by 773 days.

(21) Appl. No.: 16/406,215

(22) Filed: May 8, 2019

(65) Prior Publication Data

US 2020/0353631 A1  Nov. 12, 2020

(51) Int. Cl.
| | |
|---|---|
| *B25J 19/00* | (2006.01) |
| *B25J 9/08* | (2006.01) |
| *B25J 18/04* | (2006.01) |
| *B25J 13/00* | (2006.01) |
| *B25J 9/02* | (2006.01) |
| *A61B 17/00* | (2006.01) |

(52) U.S. Cl.
CPC ............. *B25J 19/0045* (2013.01); *B25J 9/02* (2013.01); *B25J 9/08* (2013.01); *B25J 13/006* (2013.01); *B25J 18/04* (2013.01); *A61B 2017/00345* (2013.01)

(58) Field of Classification Search
CPC . B25J 19/00; B25J 19/0045; B25J 9/08; B25J 9/02; B25J 18/04; B25J 13/006
See application file for complete search history.

(56) References Cited

U.S. PATENT DOCUMENTS

| | | | |
|---|---|---|---|
| 7,846,201 B2 | 12/2010 | Chorny et al. | |
| 8,900,293 B2 | 12/2014 | Forbes et al. | |
| 9,383,055 B2* | 7/2016 | Hirose | F16L 55/40 |
| 2011/0052393 A1* | 3/2011 | Ogrin | A61B 5/05 |
| | | | 310/38 |
| 2011/0270434 A1 | 11/2011 | Fischer | |
| 2015/0351856 A1 | 12/2015 | Choi et al. | |

(Continued)

FOREIGN PATENT DOCUMENTS

| | | |
|---|---|---|
| CN | 102686264 | 9/2012 |
| CN | 105854173 | 8/2016 |

(Continued)

OTHER PUBLICATIONS

R. Dreyfus, et al, "Microscopic artificial swimmers," Nature, vol. 437, p. 862, 2005.

(Continued)

*Primary Examiner* — Christopher J Beccia
(74) *Attorney, Agent, or Firm* — Renner Kenner Greive Bobak Taylor & Weber (57) ABSTRACT

A magnetically controllable robotic device including a body having a first body part and a second body part movably connected with the first body part. The first body part and the second body part are both rigid. The first body part is magnetically-responsive such that the first body part can be controlled by an external magnetic field generated by an magnetic control system. The first body part may be controlled such that the magnetically controllable robotic device is moved by the external magnetic field.

32 Claims, 8 Drawing Sheets

(56) References Cited

U.S. PATENT DOCUMENTS

2018/0116744 A1   5/2018  Taya
2018/0153633 A1*  6/2018  Rodriguez-Navarro ..................... A61B 34/73

FOREIGN PATENT DOCUMENTS

| CN | 107595385 | 1/2018 |
| EP | 2531220 | 5/2018 |
| EP | 3388013 | 10/2018 |

OTHER PUBLICATIONS

Z. Ye, et al, "Rotating magnetic miniature swimming robots with multiple flexible flagella," IEEE Transactions on Robotics, vol. 30, pp. 3-13, 2014.

S. Sudo, et al, "Magnetic swimming mechanism in a viscous liquid," Journal of Intelligent Material Systems and Structures, vol. 17, pp. 729-736, 2006.

I. S. Khalil, et al, "MagnetoSperm: a microrobot that navigates using weak magnetic fields," Applied Physics Letters, vol. 104, p. 223701, 2014.

I. S. Khalil, et a., "Sperm-shaped magnetic microrobots: fabrication using electrospinning, modeling, and characterization," IEEE International Conference on Robotics and Automation, pp. 1939-1944, 2016.

B. Jang, et al, "Undulatory locomotion of magnetic multilink nanoswimmers," Nano Letters, vol. 15, pp. 4829-4833, 2015.

T. Li, et al, "Magnetically propelled fish-like nanoswimmers," Small, vol. 12, pp. 6098-6105, 2016.

* cited by examiner

MAGNETICALLY CONTROLLABLE ROBOTIC DEVICE AND ITS METHOD OF MAKING

TECHNICAL FIELD

The invention relates to a magnetically controllable robotic device and a method of making a magnetically controllable robotic device. The invention also relates to a method of operating a magnetically controllable robotic device.

BACKGROUND

Robotic devices in particular microrobots for biomedical applications and research are known. Generally, these robotic devices include movement mechanism that allows the device to move along a surface, in a fluidic environment, etc. The movement mechanism may be active, e.g., driven by internal source or self-driven, or passive, e.g., driven by external source. These robotic devices can be used in various biomedical applications, including minimally invasive diagnosis, targeted delivery of drugs and cells, tissue engineering, in-vivo sensing and monitoring, etc.

WO2012148472A discloses a soft robotic actuator with a flexible body. The movement of the actuator is controlled by controlling pressurized fluid passing the flexible body. Such robotic actuator can move flexibly and can perform undulatory movement, but has relatively weak structural integrity and hence is susceptible failure in operation, especially in harsh environments posing motion resistance.

SUMMARY OF THE INVENTION

It is an object of the invention to address the above needs, to overcome or substantially ameliorate the above disadvantages or, more generally, to provide a magnetically controllable robotic device, the movement of which can be easily controlled by an external magnetic field. It is also an object of the invention to provide a magnetically controllable robotic device is particularly adapted for (but not limited to) operation in low Reynolds number (Re) regime. It is yet another of the invention to provide a simple and cost-effective method for making magnetically controllable robotic devices such as these.

In accordance with a first aspect of the invention, there is provided a magnetically controllable robotic device including a body having a first body part and a second body part movably connected with the first body part. The first body part and the second body part are both rigid. The first body part is magnetically-responsive such that the first body part can be controlled by an external magnetic field generated by a magnetic control system. The first body part may be controlled such that the magnetically controllable robotic device is moved by the external magnetic field. The movement may include translation and/or rotation in one or more directions. The magnetically controllable robotic device can be immersed in fluid (e.g., liquid).

In one embodiment of the first aspect, the second body part is movably connected with the first body part through a joint. The joint may be any form of mechanical joints, and it may enable relative rotation and/or relative translation of the first and second body parts.

Preferably, the joint is a pivot-type joint through which the second body part pivotably connects with the first body part.

In one embodiment of the first aspect, the pivot-type joint is provided partly by the first body part and partly by the second body part.

In one embodiment of the first aspect, the first body part includes a first connection portion and the second body part includes a second connection portion connected with the first connection portion. The first connection portion and the second connection portion provide the pivot-type joint.

In one embodiment of the first aspect, the first connection portion and the second connection portion are non-detachably connected with each other.

In one embodiment of the first aspect, one of the first connection portion and the second connection portion includes a rod, and the other of the first connection portion and the second connection portion defines an opening through which the rod extends. The rod may be substantially cylindrical. The opening may also be circular. The rod and the opening may be correspondingly shaped and sized such that a clearance exists between the rod and the opening.

In one embodiment of the first aspect, the first body part generally elongates along a first long axis, and the first body part is symmetric about the first long axis. Additionally or alternatively, the second body part generally elongates along a second long axis, and the second body part is symmetric about the second long axis. The first long axis and the second long axis may be collinear. The rod may extend generally orthogonal to one or both of the first long axis and the second long axis.

In one embodiment of the first aspect, the first body part includes a first arm portion and a second arm portion, arranged symmetrically about the first long axis, for interacting with the second rigid body part. The first body part is pivotable relative to the second body part between a first end position, in which the first arm portion contacts one side of the second body part, and a second end position, in which the second arm portion contacts an opposite side of the second body part. The first and second arm portions may facilitate motion transmission from the first body part to the second body part. The angle sustained by the relative angular movement between the first body part and the second body part, at the two end points, may be an acute angle, a right angle, or an obtuse angle. The acute angle may be larger than 30 degrees, larger than 45 degrees, larger than 60 degrees, etc.

In one embodiment of the first aspect, the first body part includes a portion that is formed at least partly by the first arm portion and the second arm portion. The cross section of the portion can be U-shaped, V-shaped, arc-shaped, etc.

In one embodiment of the first aspect, the body further includes a third body part movably connected with the second body part. The third body part may be movably connected with the second body part through a joint. The joint may be any form of mechanical joints, and it may enable relative rotation and/or translation of the second and third body parts. Preferably, the joint is a pivot-type joint through which the third body part pivotably connects with the second body part. The pivot-type joint may be provided partly by the second body part and partly by the third body part. The third body part includes a third connection portion and the second body part includes a further second connection portion connected with the third connection portion. The third connection portion and the further second connection portion cooperate to provide the pivot-type joint. The third connection portion and the further second connection portion are non-detachably connected with each other. One of the third connection portion and the further second connection portion includes a rod, and the other of the third connection portion and the further second connection portion defines an opening through which the rod extends. In one embodiment, one of the second connection portion and the further second connection portion includes a rod, and the other of the second connection portion and the further second connection portion defines an opening through which the rod extends. The rod may be substantially cylindrical. The opening may be cylindrical. The rod and the opening may be correspondingly shaped and sized such that a clearance exists between the rod and the opening. The third body part may generally elongate along a third long axis, and the third body part is symmetric about the third long axis. The third long axis and the second long axis may be collinear. The second body part may include a first arm portion and a second arm portion, arranged symmetrically about the second long axis. The second body part may be pivotable relative to the third body part between a first end position, in which the first arm portion contacts one side of the third body part, and a second end position, in which the second arm portion contacts an opposite side of the third body part. The angle sustained by the relative angular movement between the second body part and the third body part, at the two end points, may be an acute angle, a right angle, or an obtuse angle. The acute angle may be larger than 30 degrees, larger than 45 degrees, larger than 60 degrees, etc.

In one embodiment of the first aspect, the body further includes a fourth body part movably connected with the third body part. The fourth body part may have the same construction as the second body part or the third body part. Preferably, the body is made up entirely of rigid body parts that are movably connected with each other.

In one embodiment of the first aspect, the magnetically-controlled robotic device further includes magnetically-responsive material arranged on at least part of a surface of the first body part that makes the first body part magnetically-responsive. The magnetically-responsive material may alternatively or additionally be arranged in at least part of the first body part.

In one embodiment of the first aspect, the magnetically-responsive material is in the form of a coating arranged on at least part of the first body part such that the first body part is magnetically-responsive.

In one embodiment of the first aspect, the magnetically-responsive coating is arranged on only part of the first body part. For example, the joint may be devoid of magnetically-responsive material or magnetically-responsive coating. In one example, the magnetically-responsive material is the only magnetically-responsive material in the entire robotic device.

In one embodiment of the first aspect, the first body part and the second body part are integrally formed. The first body part and the second body part may be made from photo-curable material. Example of the photo-curable material includes: polymer, ceramics, nanofiber, or any of their combination. The photo-curable material may include any of the following photoresist: SU-8 polymer, IP-L, IP-G, and any of their combination. One specific example is IP-L 780.

In one embodiment of the first aspect, the first body part is the only magnetically-responsive part of the magnetically controllable robotic device.

In one embodiment of the first aspect, the magnetically-responsive coating contains metal. Example of the metal includes: nickel, iron, cobalt, neodymium, or any of their combination.

In one embodiment of the first aspect, the magnetically controllable robotic device is tetherless.

In one embodiment of the first aspect, the magnetically controllable robotic device is a micro-robotic device for biomedical applications. The biomedical applications may be in vivo or in vitro. In one example, the micro-robotic device may have a length in the order of microns (preferably, tens, hundreds, or thousands of microns).

In accordance with a second aspect of the invention, there is provided a method for making a magnetically controllable robotic device, including forming a body having a first body part and a second body part movably connected with the first body part; and arranging the first body part to be magnetically-responsive such that the first body part can be controlled by an external magnetic field generated by an magnetic control system. The magnetically controllable robotic device may be the one of the first aspect.

In one embodiment of the second aspect, arranging the first body part to be magnetically-responsive includes applying magnetically-responsive material on at least part of a surface of the first body part.

In one embodiment of the second aspect, the magnetically-responsive material is arranged in the form of a magnetically-responsive coating on at least part of a surface of the first body part.

In one embodiment of the second aspect, the application of magnetically-responsive material on at least part of a surface of the first body part is performed using electron beam deposition, dipping, electroplating, sputtering, or chemical vapor deposition.

In one embodiment of the second aspect, the method also includes shielding other parts of the body when magnetically-responsive material or coating is applied on at least part of a surface of the first body part. As a result, the other parts of the body are not applied with magnetically-responsive material.

In one embodiment of the second aspect, the magnetically-responsive coating is arranged on only part of a surface of the first body part.

In one embodiment of the second aspect, the magnetically-responsive material contains metal. Examples of the metal includes: nickel, iron, cobalt, neodymium, or any of their combination.

In one embodiment of the second aspect, forming the body includes integrally forming the body with the first body part and the second body part. The integrally formed first and second body parts are not detachable.

In one embodiment of the second aspect, forming the body includes performing laser lithography on a photo-curable material to form the body. The body can be 3D-printed using a 3D printing apparatus.

In one embodiment of the second aspect, the photo-curable material includes: polymer, ceramics, nanofiber, or any of their combination. The photo-curable material may include any of the following photoresist: SU-8 polymer, IP-L, IP-G, and any of their combination. One specific example is IP-L 780.

In accordance with a third aspect of the invention, there is provided a magnetic control system for controlling a magnetically controllable robotic device, including: two or more magnets spaced apart and defining a space between them for receiving the magnetically controllable robotic device. The two or more magnets are arranged to interact with the magnetically controllable robotic device arranged in the space to, e.g., control its movement. The two or more magnets may include permanent magnets and/or electromagnets.

In one embodiment of the third aspect, the two or more magnets is supported by and/or mounted in or on a frame, platform, or housing, which also defines the space.

In one embodiment of the third aspect, the magnetic control system further includes a container arranged in the space. The container defines a chamber for receiving the magnetically controllable robotic device. The container may also receive fluid (e.g., liquid), in which the magnetically controllable robotic device can be arranged. The two or more magnets are preferably arranged around the container. The two or more magnets may be evenly distributed around the container. In one example, the two or more magnets may be angularly distributed around the container such that the two or more magnets lie on an imaginary circle.

In one embodiment of the third aspect, the magnetic control system further includes a motor; and the frame, platform, or housing supporting the two or more magnets is operably connected to the motor to be moved by the motor.

In one embodiment of the third aspect, the motor is arranged to rotate the frame, platform, or housing about an axis. The rotation may be clockwise only, anti-clockwise only, or both. Preferably, the motor is arranged to oscillate the frame, platform, or housing about the axis.

In one embodiment of the third aspect, the magnetic control system further includes a controller for controlling operation of the motor to effect movement of the frame, platform, or housing. The controller may control the motor to affect the frequency and/or amplitude of the movement of the platform. Preferably, the controller is arranged to control the motor to oscillate the platform with simple harmonic motion.

In one embodiment of the third aspect, the two or more magnets include two diametrically opposed magnets. The two diametrically opposed magnets are accurate. Each of the two diametrically opposed magnets has concave face facing each other. The concave face may be of opposite magnetic polarities.

In one embodiment of the third aspect, the magnetic control system further includes one or more mounts each for mounting a respective magnet. The one or more mounts may be movable. For example, in one embodiment in which the two or more magnets include two diametrically opposed magnets each mounted in or on a respective mount, the mounts are movable to adjust a separation (diametric, angular, etc.) between the two diametrically opposed magnets.

In one embodiment of the third aspect, the magnetic control system further includes an imaging device for imaging the magnetically controllable robotic device in the chamber. The imaging device may be a CCD camera. The imaging device and the controller of the motor may be operably connected such that the controller of the motor operates based on feedback from the imaging device.

In accordance with a fourth aspect of the invention, there is provided a method for operating a magnetically controllable robotic device, comprising: applying an external magnetic field to a space in which the magnetically controllable robotic device is arranged; and changing the external magnetic field generated to control movement of the magnetically controllable robotic device. The magnetically controllable robotic device may be the one of the first aspect, or one that is formed using the method of the second aspect. The application of the external magnetic field may be performed by the magnetic control system of the third aspect. Preferably, changing the external magnetic field includes controlling the external magnetic field to be an oscillating magnetic field. Preferably, the oscillating magnetic field is a uniformly oscillating magnetic field.

In accordance with a fifth aspect of the invention, there is provided a magnetically controllable robotic device made using the method of the second aspect.

In accordance with a sixth aspect of the invention, there is provided a kit containing the magnetically controllable robotic device of the first aspect, and the magnetic control system of the third aspect.

In accordance with a seventh aspect of the invention, there is provided a kit containing the magnetically controllable robotic device made using the method of the second aspect, and the magnetic control system of the third aspect.

BRIEF DESCRIPTION OF THE DRAWINGS

Embodiments of the invention will now be described, by way of example, with reference to the accompanying drawings in which.

DETAILED DESCRIPTION OF THE PREFERRED EMBODIMENT

Figure 1A:
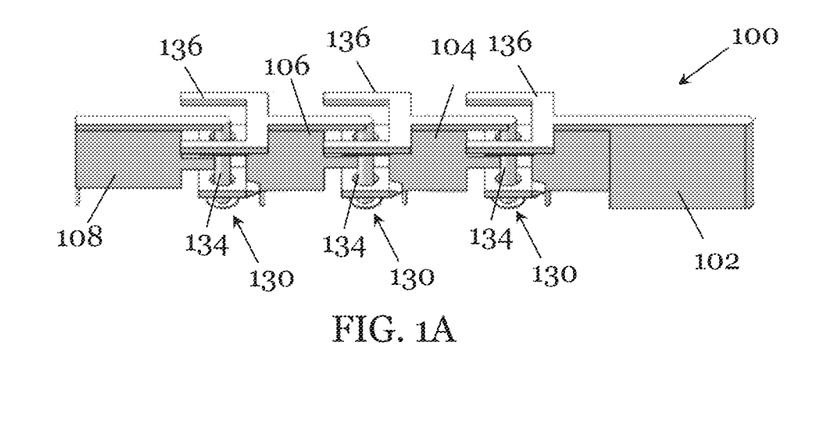
FIG. 1A is a perspective view of a magnetically controllable robotic device in one embodiment of the invention.
Figure 1B:
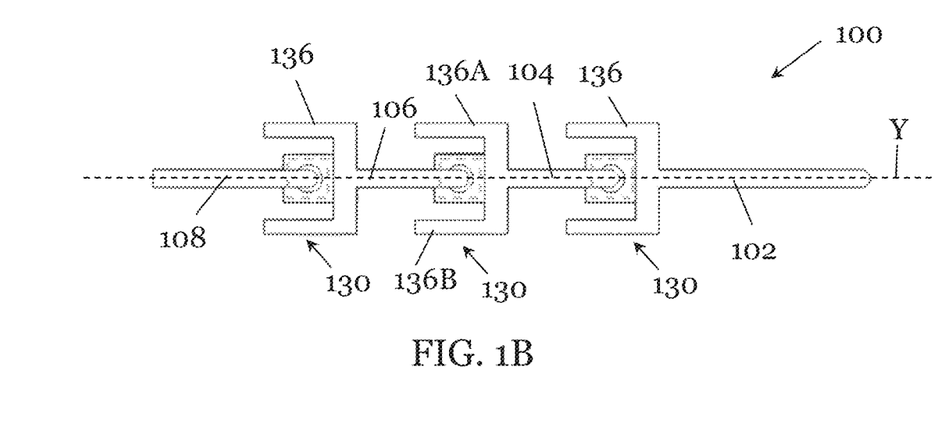
FIG. 1B is a top plan view of the magnetically controllable robotic device of FIG. 1A.
Figure 1C:
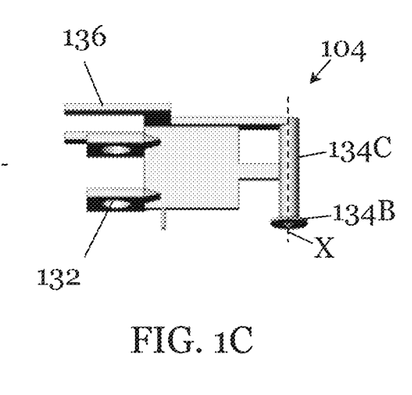
FIG. 1C is a perspective view of one of the body parts of the magnetically controllable robotic device of FIG. 1A.

FIGS. 1A to 1C show a magnetically controlled robotic device 100 in one embodiment of the invention. The device 100 includes a body with a first body part 102 (also referred to as "head"), a second body part 104 movably connected with the first body part 102, a third body part 106 movably connected with the second body part 104, and a fourth body part 108 (also referred to as "tail") movably connected with the third body part 106. The first body part 102 is partly coated with a magnetic responsive material. The magnetic responsive material hence the first body part 102 can be controlled by an external magnetic control system that generates an external magnetic field. The external magnetic field interacts with the magnetic responsive material to move the first body part hence the robotic device 100. More specifically, by applying the external magnetic field, movement of the head 102 can be controlled, and the movement of the head 102 is transmitted to the body part 104, then to the body part 106, and in turn to the tail 108, through transmission mechanisms arranged between adjacent body parts. The robotic device 100 can travel in different directions, and can travel generally along a single direction by creating a traveling wave to generate undulatory propulsion in the low Re regime, under the interaction with the external magnetic field. In this embodiment, the robotic device 100 is integrally made of a single material formed integrally using 3D printing technology. The material can be a photo-curable polymer, ceramics or nanofiber which is cured upon exposure of light, details of which will be discussed below.

Referring to FIGS. 1A to 1C, the movable connection between adjacent body parts is achieved through a movable joint 130 arranged between every two adjacent body parts (i.e., head 102 and tail 108 only has one joint 130, while all intermediate body parts 104, 106 have two joints 130 at opposite ends). The movable joint 130 is partly ion formed by one body part and partly formed by an adjacent body part. The joint 130 permits relative movement between adjacent body parts, hence enabling an undulatory locomotion.

In this embodiment, the joint 130 is defined by two identical openings 132 on a side of one body part, and a rod 134 on an opposite side of the same body part. The two openings 132 of one body part are arranged to receive the rod 134 of the adjacent body part. The openings and the rod arranged to be received in the openings are correspondingly shaped. The openings and the rod are sized such that a small clearance exists between the openings and the rod. In this way, adjacent body parts of the body of the robotic device 100 are linked together by use of the rod 134 and the opening 132 of the joints 130.

FIG. 1C illustrates the construction of the second body part 104. It should be noted that the rod 134 in the second body part 104 is for receiving in the corresponding openings (like openings 132) in the head 102, and the openings 132 in the second body part 104 are for receiving a corresponding rod 134 in the third body part 106. It should be appreciated that the constructions of the rod, the opening, or both can be applied to the other body parts to form the joint 130.

In FIG. 1C, the rod 134 of the second body part 104 is in the form of a stanchion with a cylindrical part 134C elongating along an axis X, and an enlarged circular flat base 134B connected at an end of the cylindrical part. The openings 132 are provided in two spaced-apart parallel plate portions extending from a side of the body part 104. The openings 132 are circular and are generally axially aligned. Each of the openings 132 is designed with a diameter larger than the diameter of the cylindrical part of the rod of the adjacent body part, yet smaller than the diameter of the base of the rod of the adjacent body part so that the rod is non-detachably received within the openings 132. The clearance between the rod and the openings permit relative pivot movement of adjacent body parts, as well as slight relative translational movement of adjacent body parts.

The body parts 102, 104, 106 also include a motion transferring portion 136 having a generally U-shaped cross section (in plan view of FIG. 1B) for transferring motion to the respective adjacent body parts 104, 106, 108. Take the body part 104 in FIG. 1C as an example, the motion transferring portion 136 is arranged above the two plates forming the openings 132 for transferring motion to the adjacent body part 106. The motion transferring portion 136 includes a first arm portion 136A and a second arm portion 136B, arranged symmetrically about the long axis Y, for interacting with the other body part 106. The first arm portion 136A elongates generally parallel to the long axis Y. The second arm portion 136B also elongates generally parallel to the long axis Y. The body part 104 is pivotable relative to the body part 106 between a first end position, in which the first arm portion 136A contacts a side of the other body part 136, and a second end position, in which the second arm portion 136B contacts an opposite side of the other body part 106. The contact of first and second arm portions 136A, 136B with the other body part 106 facilitate motion transmission from the body part 104 to the body part 106. The motion transferring portion 136 of other body parts 102, 106 can function in a similar manner. In this example, the motion transferring portion 136 can also limit the angle of relative movement of the rod and the opening of adjacent body parts to limiting relative angular movement of the adjacent body parts for an effective undulatory locomotion. Thus, under external magnetic actuation, the oscillating motion of the head 102 is transferred from the head 102 to the body part 104, then from the body part to the body part 106, then from the body part 106 to the tail 108. This generates a traveling-wave propulsion to propel the robotic device 100 to move forward, in particular in an environment of the low Re regime.

If the body parts 102, 104, 106 are made without the motion transferring portion 136, the friction between each body part may in some cases be insufficient to drive the adjacent body part, and as a result traveling-wave propulsion for the robotic device 100 may become less effective if not completely ineffective.

Figure 2A:
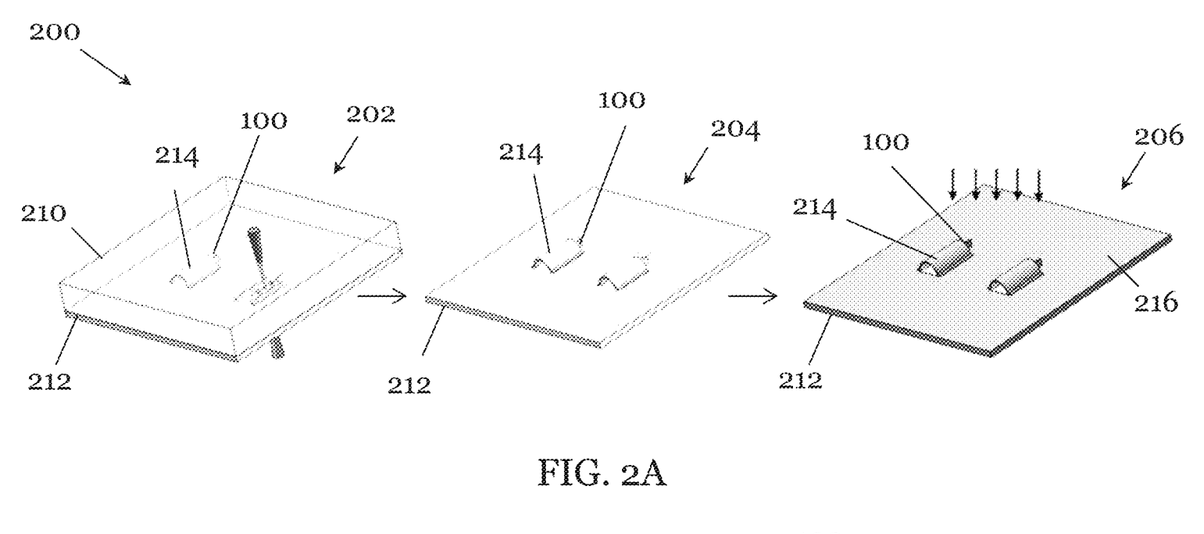
FIG. 2A is a schematic flow diagram illustrating a method for making a magnetically controllable robotic device of FIG. 1A.

FIG. 2A shows a general method 200 of making a magnetically controlled robotic device such as the magnetically controlled robotic device 100 FIGS. 1A to 1C. For simplicity and ease of presentation, the method 200 will be discussed below with reference to the robotic device 100.

First, in step 202, the body of the robotic device 100 including the first and second body parts 104, 106 is formed such that the second body part 104 is movably connected with the first body part 102. In this step 202, a resin material 210 may be first provided on top of a substrate 212, or alternatively, the substrate 212 may be provided at a later stage. The resin material 210 is preferably a photo-curable material such as SU-8 polymer, IP-L, IP-G, or any combination thereof. Different body parts of the robotic device too are formed integrally as a single component using 3D laser lithography. Alternatively, each body part may be formed separately and connected, integrated, or otherwise joint together afterwards. In one example, each of the joints 130 may be formed as a separate component and not as part of the body parts. The step 202 further includes providing a sacrificial shielding structure 214 to cover the parts of the body other than the head 102 to which magnetic responsive material is to be applied in step 206 (to be explained below). The sacrificial shielding structure 214 may be formed integrally with the body of the robotic device 100 using 3D laser lithography, or it may be formed as a separate component using 3D laser lithography, or other means, for shielding the remainder of the body of the robotic device 100.

In step 204, the developing step, the photo-curable material 210 allows the flexible material to polymerize and conform into a hardened material as it is cured upon exposure to light, forming the desired rigid structure. The unwanted, polymerized resin material 210 is then removed from the substrate 212.

Figure 2B:
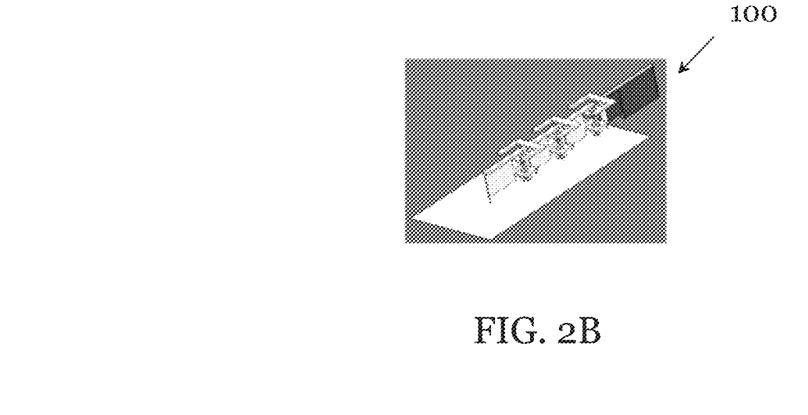
FIG. 2B is a perspective view of the magnetically controllable robotic device made using the method of FIG. 2A (and which is hidden from view in FIG. 2A)

In step 206, a magnetic responsive material 216 is applied to part of the body of the robotic device 100 to enable the robotic device 100 (its movement) to be controlled with a magnetic control system. Preferably, the magnetic responsive material 216 is a relatively non-corrosive metal including nickel (Ni), iron (Fe), cobalt (Co), neodymium (Nd), or any combination thereof. In this embodiment, a layer of magnetic responsive material 216 is deposited on the robotic device 100 and the substrate 212. As shown in FIG. 2B, because of the sacrificial shielding structure 214 shields the body parts of the robotic device 100 that are not to be deposited with magnetic responsive material, the layer of magnetic responsive material 216 is only coated on the part of the head 102 of the robotic device 100 that is exposed. In other embodiments, the magnetic layer 216 may alternatively be coated on other body parts of the robotic device 100 such that the movement of the robotic device 100 is controlled at a different location of the body. The coating method 200 may include electron beam deposition, dipping, electroplating, sputtering, or chemical vapor deposition. At the end of the method 200, the sacrificial shielding structure 214 is removed and discarded, and the robotic device is removed from the substrate 212 for use.

In this embodiment, the method 200 is performed using a commercial 3D printing system in IP-L 780 as the photo-curable resin material 210 on a glass substrate 212 with an oil immersion objective of 63xNA1.4. The 3D printing technology based on the two-photon polymerization principle allows the rapid manufacture of samples with complex geometry, and is ideal for making the robotic device 100 with different body parts connected through joints. IP-L 780 is a liquid negative-tone photoresist which provides the end product (i.e., the robotic device body) with high resolution, low shrinkage and high stability. The structures made of IP-L 780 also exhibit great robustness and ability to maintain their shapes during fabrication. In FIG. 2A, in step 202, multiple robotic devices 100 (each having a head 102, a first body 104, a second body 106 and a tail 108), and respective sacrificial shielding structure 214 (shielding the respective robotic device 100) are directly formed in the IP-L 780 using 3D laser lithography. In step 204, the printed robotic devices 100 are developed, and conformed into hardened polymerized structures upon exposure to light. Following the developing step, the unpolymerized photoresist (i.e. the IP-L 780) is removed using propylene glycol methyl ether acetate (PGMEA), leaving only the rigid structures on the glass substrate 212. In step 206, a Ni layer 216 is deposited on the robotic devices 100 and the glass substrate 212 using a sputtering system. With the use of the sacrificial shielding structure 214, only part of the head 102 of the robotic device 100 is deposited with the Ni layer 216 for interacting with a magnetic field applied by a magnetic control system. Afterwards, the sacrificial shielding structure 214 is removed from the glass substrate 212 using a laboratory-designed micro-probe operation platform and the robotic device 100 is detached from the glass substrate 212, forming the robotic device 100.

Figure 3A:
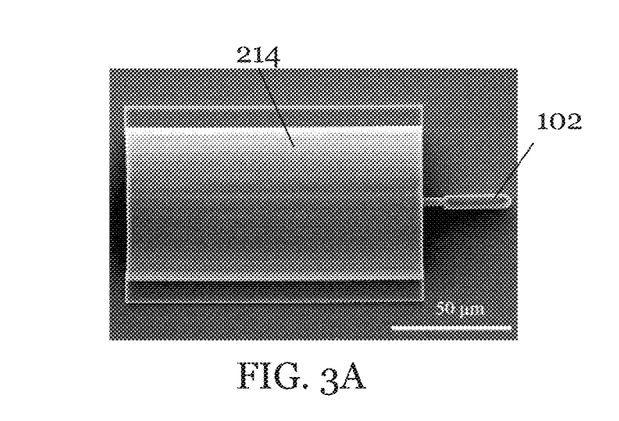
FIG. 3A is a scanning electron microscopy (SEM) image of in one step of the method of FIG. 2A, in which the magnetically controllable robotic device is hidden from view by a shielding, sacrificial shielding structure.
Figure 3B:
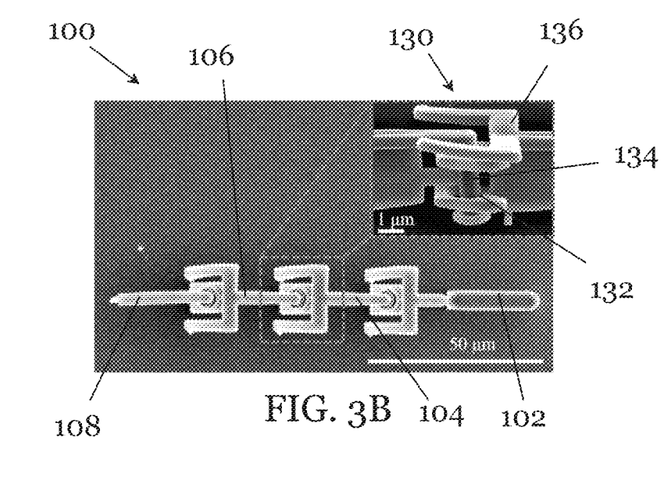
FIG. 3B is a scanning electron microscopy (SEM) image of the magnetically controllable robotic device made using the method of FIG. 2A.
Figure 3C:
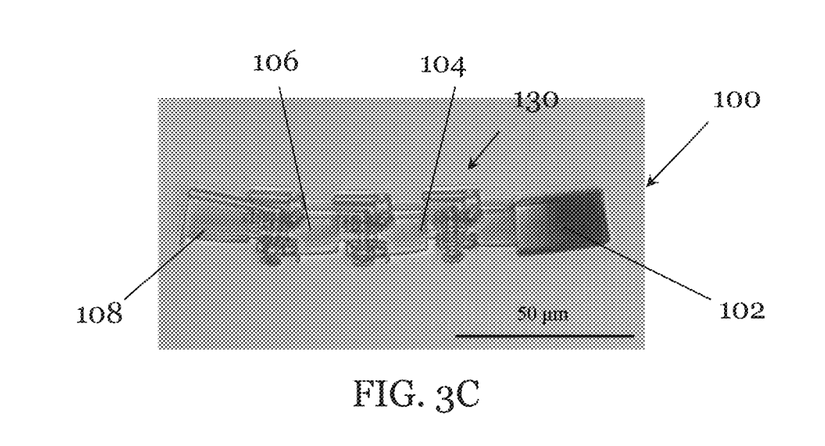
FIG. 3C is an optical microscopy image of the magnetically controllable robotic device made using the method of FIG. 2A.

FIGS. 3A and 3B are SEM images of a fabricated robotic device 100 in accordance to one embodiment. FIG. 3A shows the top view of the sacrificial shielding structure 214 covering all body parts apart from the part of the head 102 to which magnetic-responsive material is to be applied (after step 206 before the removal from the substrate 212). As discussed above, the sacrificial shielding structure 214 is designed to protect the remaining body parts from the deposition of the magnetic layer 216 such that only the head 102 is magnetized and the undulatory locomotion is achieved and controlled by the external magnetic field. FIG. 3B shows the robotic device 100 after the removal of the sacrificial shielding structure 214. As shown in FIG. 3B, the first body part 104 is substantially identical to the second body part 106, both having substantially the same length and substantially the same structure, and are linked together by the joint 130. FIG. 3B also shows an enlarged side view of the joint 130, together with the motion transferring portion 136. It can be seen that the motion transferring portion 136 partially surrounds the rod 134 of the joint 130, thus limiting the angle movement of the rod 134. The head 102 of the robotic device 100 as shown has a relative long length compared to the other body parts. In this embodiment, the length of the head 102 is about 50 μm, while the individual length of each of the remaining body parts is about 30 μm. As shown in FIG. 3C, the head 102 also has a height of about 17 μm. The long length and the height of the head 102 allow the head 102 to obtain more magnetism during the fabrication process, specifically in step 206. It will be appreciated by the skilled person that the length of each of the body parts may be more than or less than 30 μm, but generally the length of the body part which is coated with the magnetic-responsive material layer 216 is relatively long so that more magnetism is obtained. FIG. 3C also shows the microscopic image of the robotic device 100 after the deposition of the magnetic-responsive material 216, which is the Ni layer 216 in this embodiment. In this embodiment, only part of the head 102 of the robotic device 100 is deposited with Ni layer 216. The other parts are not deposited with magnetic-responsive material due to the use of the sacrificial shielding structure 214.

Figure 4A:
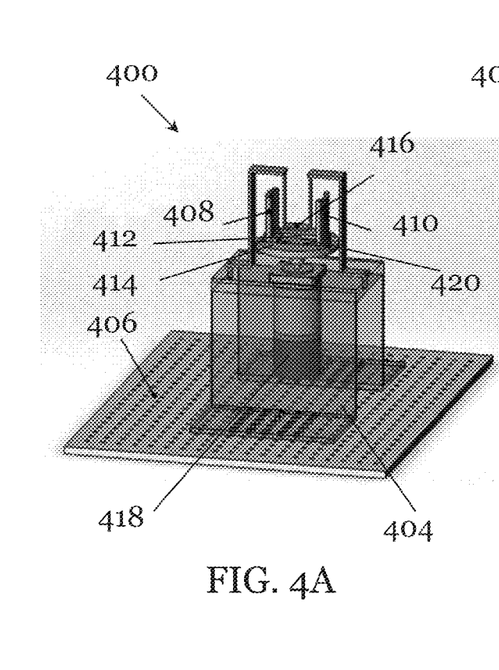
FIG. 4A is a schematic diagram showing a magnetic control system for controlling a magnetically controllable robotic device in one embodiment of the invention.

FIG. 4A shows a magnetic control system 400 for controlling movement of a robotic device, such as the magnetically-controllable robotic device. For simplicity and ease of presentation, the system 400 will be discussed with reference to the robotic device 100.

The system 400 includes a portable power supply 402. The system 400 includes a stand 404 on top of a base 406 at the bottom arranged to support the other components of the magnetic control system 400. The other components supported by the stand 404 includes two magnets 408, 410, two movable clamps 412 for clamping each of the magnets 408, 410, a platform 414 arranged to oscillate and support the clamps 412 and the magnets 408, 410, a sample stage 416 positioned between the two magnets 408, 410 and above the platform 414, and a DC motor 418 for oscillating the platform 414. The platform 414 has a generally circular cross section in plan view.

Figure 4B:
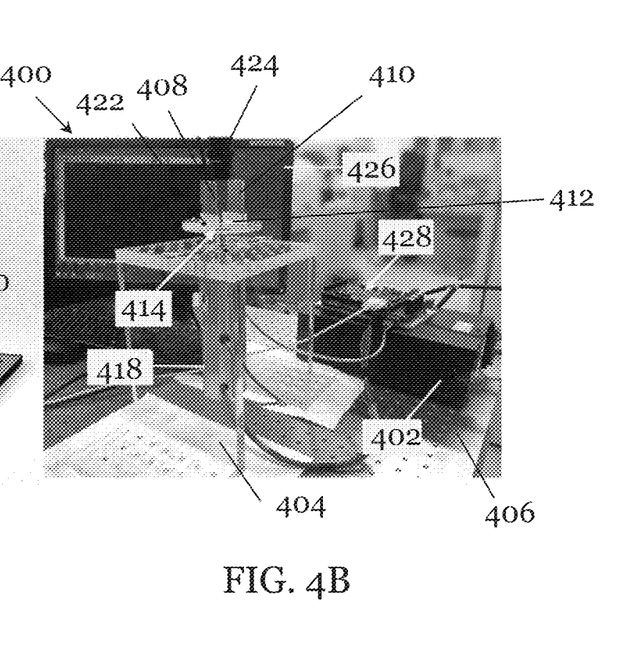
FIG. 4B is a picture showing a magnetic control system for controlling a magnetically controllable robotic device constructed based on the magnetic control system of FIG. 4A in one embodiment of the invention.

FIG. 4B shows the assembled magnetic control system 400. As shown in FIG. 4B, the two magnets 408, 410 are arcuate and are diametrically opposed. The magnets are Nd magnets 408, 410 for generating a uniform magnetic field. The two magnets 408, 410 are arranged facing each other with an opposite polarity so as to generate attraction in one direction and repulsion in another direction, thus allowing the movement of the robotic device 100. The platform 414 has a channel 420 in the center along which the movable clamps 412 can slide such that the distance between the two magnets 408, 410 is adjustable using the movable clamps 412. This in turns allows a user to manipulate the magnetic field strength applied to the robotic device 100, for example, to control the speed of forward movement of the robotic device 100. A stop 422 is provided on each end of the channel 420 of the platform 414. The stop 422 is arranged to abut the movable clamps 412 and to prevent the clamps 412 to move out of the channel 420. The platform 414 is operably connected with the motor 418 and is driven by the motor. The DC motor 418 is driven by a motor controller 428 and configured to control the oscillation of the platform 414 with controlled frequency and amplitude. The DC motor 418 can oscillate the platform 414 with a simple harmonic motion (SHM) in one application.

To use the magnetic control system 400 to control the magnetically controllable robotic device 100, the magnetically controllable robotic device 100 is first placed in a chamber of deionized water (not shown) on the sample stage 416. The oscillating platform 414 with the magnets 408, 410 allow the magnetically controllable robotic device 100 to follow the oscillating motion of the magnetic field applied by the magnets 408, 410, to oscillate periodically, and to achieve the desired undulatory propulsion with a net forward movement. The system 400 further includes a camera 424 and a computer 426 for producing visual feedback, which is particularly useful in some biomedical applications. The camera 424 may be a CCD camera.

Figure 5A:
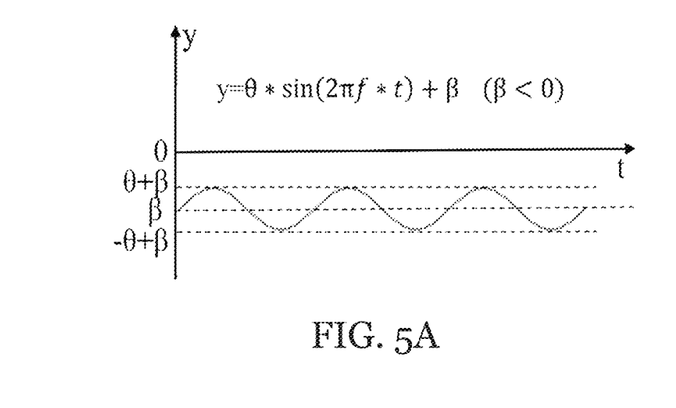
FIG. 5A is a graph showing the variation of angles of movement when the magnetically controllable robotic device of FIG. 1A is controlled by a magnetic control system in one embodiment of the invention.
Figure 5B:
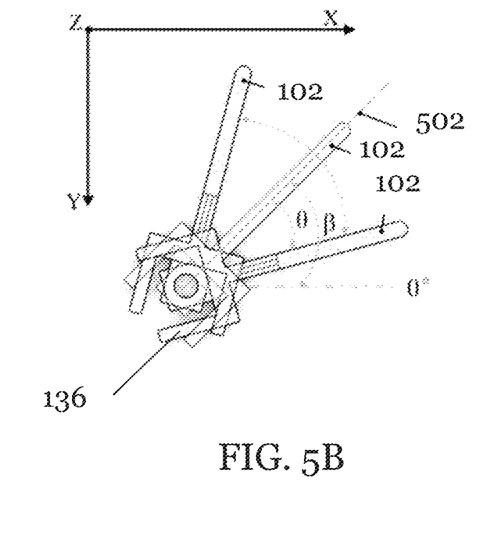
FIG. 5B is a schematic plot showing the movement of the head of the robotic device corresponding to the graph of FIG. 5A.

As the platform 414 oscillates, the head 102 of the robotic device 100 placed on the sample stage 416 also can exhibits a simple harmonic motion (SHM). The movement of the robotic device 100 is demonstrated using the head 102 of the robotic device 100, as shown in FIGS. 5A and 5B. A central axis 502 of the oscillating motion of the head 102 is defined by the direction of net forward movement of the head 102. An offset angle β, which is used to indicate the direction of net forward movement, is defined between the central axis 502 and the positive X-axis (0 degrees) as shown. The offset angle β from the positive X-axis to the central axis 502 in the clockwise direction is defined as a positive value, while the offset angle β from the central axis 502 to the positive X-axis in the clockwise direction is defined as a negative value. An angle θ, is defined by the displacement of the oscillating motion from the central axis 502, where a positive value is defined in the clockwise direction from the central axis 502, and a negative value is defined in the anti-clockwise direction from the central axis 502.

Upon applying the external magnetic field using the magnetic control system 400, the head 102 of the robotic device 100 oscillates with an SHM, as shown in FIG. 5A. The amplitude of the SHM is indicated by the maximum displacement (i.e. the difference between the positive and negative values of the angle θ) of the oscillating motion of the robotic device 100. Referring to FIG. 5B, the direction of net forward movement of the head 102 is indicated, by the arrow, along the central axis 502 towards the upper right. The offset angle β is measured from the central axis 502 to the positive X-axis in the clockwise direction, and therefore has a negative value. The offset angle β can be adjusted by the user using the external magnetic control system 400. As discussed above, this can be achieved by the controlling the frequency and amplitude of the oscillation of the platform 414 using the motor 418 and the motor controller 428. By changing the offset angle β, the head 102 thus the entire body of the robotic device 100 can be controlled to move in different directions in a 2D plane.

FIGS. 6A to 6D are images showing the undulatory motion of the magnetically controllable robotic device 100 at different times under an external oscillating uniform magnetic field applied by the system 400 of FIG. 4B. The motion of the head 102 is indicated by the curved arrow, the central axis 502 is indicated by the linear dotted lines, the general direction of travel of the device 100 is indicated by the thick straight arrow. The direction of net forward movement is defined along the arrow with an offset angle β of 0°.

Figure 6A:
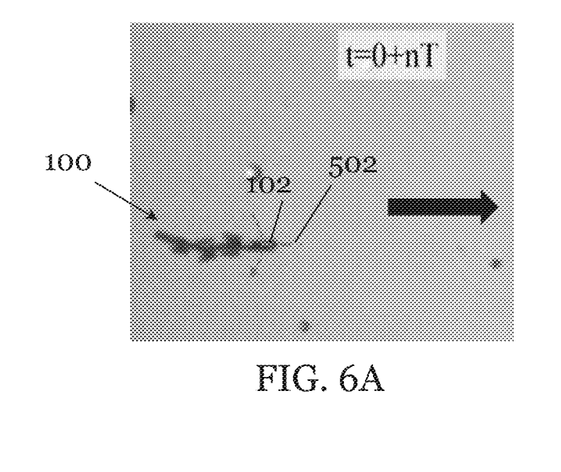
FIG. 6A is a picture illustrating position and orientation of the magnetically controllable robotic device of FIG. 3C controlled by the magnetic control system of FIG. 4B at a first time point in an experiment.
Figure 6B:
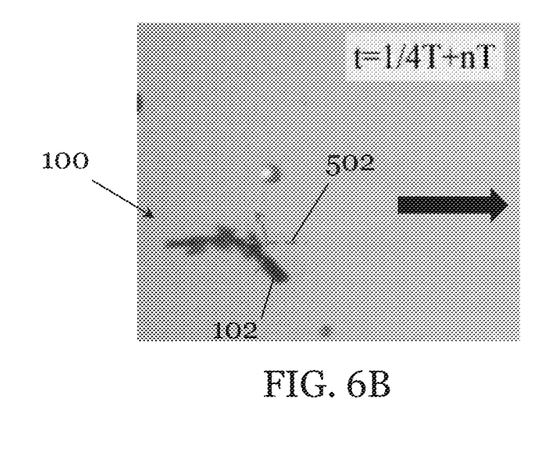
FIG. 6B is a picture illustrating position and orientation of the magnetically controllable robotic device of FIG. 3C controlled by the magnetic control system of FIG. 4B at a second time point in the experiment.
Figure 6C:
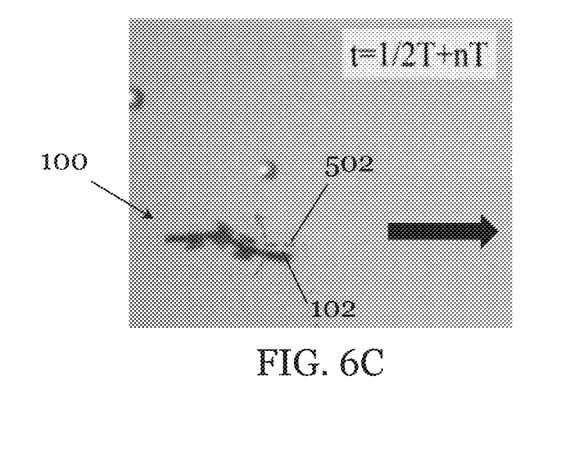
FIG. 6C is a picture illustrating position and orientation of the magnetically controllable robotic device of FIG. 3C controlled by the magnetic control system of FIG. 4B at a third time point in an experiment.
Figure 6D:
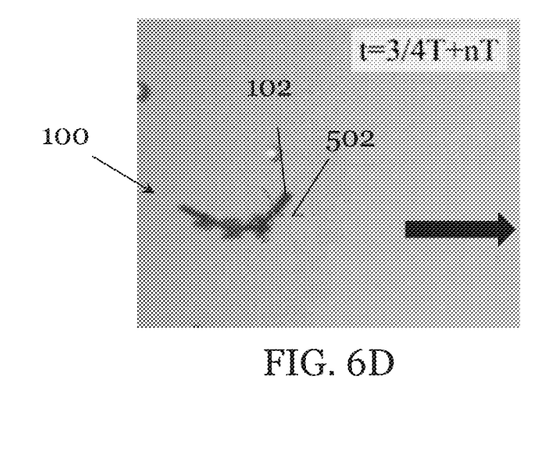
FIG. 6D is a picture illustrating position and orientation of the magnetically controllable robotic device of FIG. 3C controlled by the magnetic control system of FIG. 4B at a fourth time point in an experiment.

FIGS. 6A to 6D show oscillation of the head 102 as time varies. At the starting position as shown in FIG. 6A, the length of the head 102 is aligned with the central axis 502, thus the direction of net forward movement. As the platform 414 of the magnetic control system 400 starts oscillating by the motor 418, the magnets 408, 410 of the system 400 also start oscillating with the same pattern as the platform 414. This in turns causes the magnetically-coated head 102 of the robotic device 100 to oscillate with the same pattern. FIGS. 6B and 6D demonstrate the SHM of the head 102, showing an oscillation amplitude of about +45° and −45°, respectively, at different time instants. The experimental results demonstrate that the 3D structure of the robotic device 100 with multiple rigid body parts can oscillate and hence travel generally along a direction.

Figure 7:
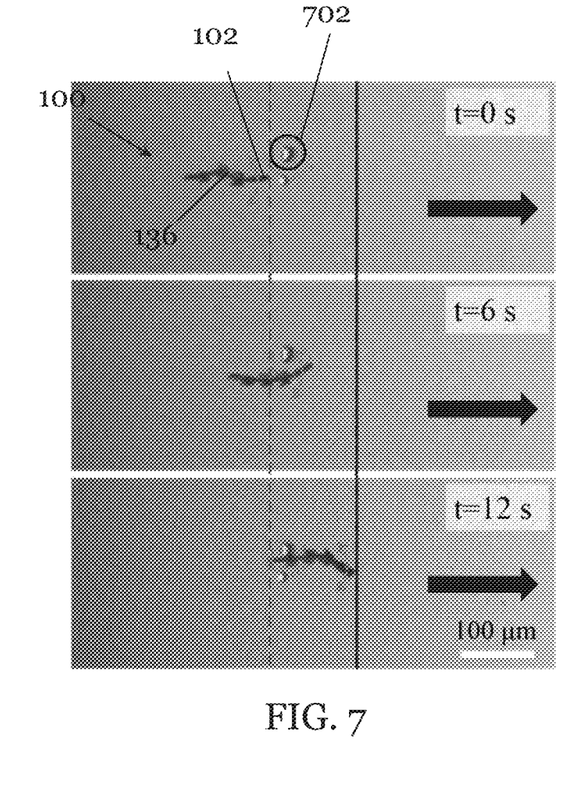
FIG. 7 is a series of images taken at different time points showing movement of the magnetically controllable robotic device of FIG. 3C controlled by the magnetic control system of FIG. 4B.
Figure 8:
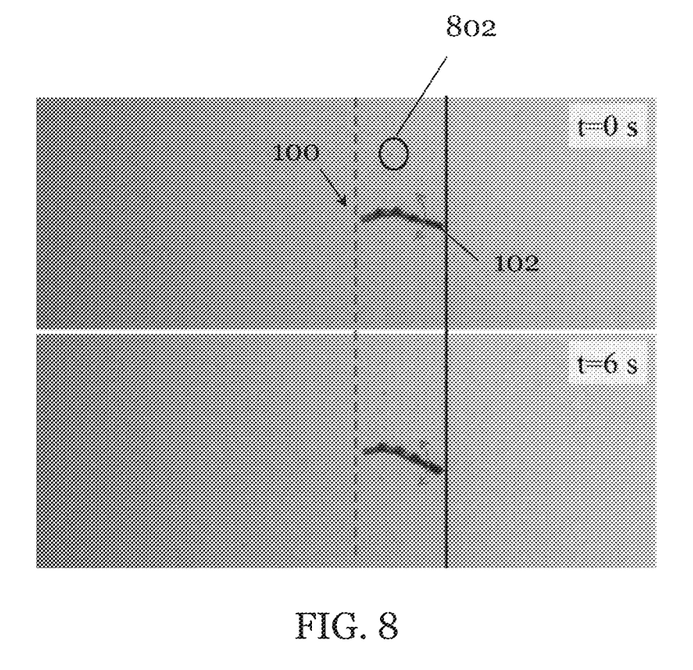
FIG. 8 is a series of images taken at different time points showing movement of a magnetically controllable robotic device modified from FIG. 3C (with the transmission mechanism removed) controlled by the magnetic control system of FIG. 4B.

FIGS. 7 and 8 show the free-swimming performances of the robotic device 100 with motion transferring portions 136 (FIG. 7) and without motion transferring portion 136 (FIG. 8) under an external oscillating uniform magnetic field (applied by the system 400). The vertical dotted line indicates the starting point of the robotic device 100, while the vertical solid line indicates the end point of the robotic device 100. These experimental results illustrate the importance of the motion transferring portion 136s of the robotic device 100. As shown in FIG. 7, the robotic device 100 with motion transferring portions 136 is able to move along a direction indicated by the arrow, when compared with the reference point 702. It is also shown that the oscillation motion of the head 102 is transferred to the other body parts. The experiment demonstrates that the robotic device 100 can break the time-reversal symmetry and achieve a net propulsion at a distance of about 100 μm within 12 seconds by using undulatory locomotion along the direction guided by the externally magnetic oscillating field generated by the magnetic control system 400, allowing a non-reciprocal motion in the low Re regime.

On the other hand, the robotic device 100 without motion transferring portions 136 is less capable of moving forward under an external actuation. As shown in FIG. 8, the robotic device 100 does not move forward by much in 6 seconds (when compared to the reference point 802, which can be a mark on the container holding the device 100). In the absence of the motion transferring portions 136, the oscillating motion of the head 102 cannot be effectively transferred to the adjacent body parts 104, 106, 108. Since there is no undulatory motion, no traveling-wave propulsion is generated along each body part, thus causing an absence of the net forward movement of the robotic device 100.

The above embodiments of the invention have provided a robotic device with a body made of a single, rigid material which provides improved structural integrity compared with the soft body robotic devices which are mainly made of soft materials. Also, the robotic device of the above embodiments can be made cheaply and simply, especially when compared with soft body robotic devices containing soft or flexible components, which require relatively sophisticated fabrication process to make. In some embodiments, the robotic device of the invention can be fabricated utilizing 3D laser lithography rapidly and precisely. The robotic device of some embodiments can break the time-reversal symmetry and achieve net propulsion, which is particular suited for use in the low Re regime.

It will be appreciated by persons skilled in the art that numerous variations and/or modifications may be made to the invention as shown in the specific embodiments without departing from the spirit or scope of the invention as broadly described. The described embodiments of the invention should therefore be considered in all respects as illustrative, not restrictive. The illustrated method for making a robotic device can be used to make a robotic device different from that illustrated. The illustrated robotic device or any robotic device made using the illustrated method can be controlled by any type of external magnetic control system, not necessarily the magnetic control system illustrated. Likewise, the magnetic control system illustrated can be used to control robotic device other than that illustrated.

For example, the body of the robotic device may be formed by two or more (any number, not necessarily four) rigid body parts movably connected with each other. The different body parts may be shaped and sized differently than those shown and illustrated in the above embodiments. The body parts is generally elongated and can be in the form of a cuboid, cylinder, an ellipsoid, a circular cone, etc., depending on the specific application of the robotic device. In one example, the body may include one or more body parts having a holder for holding a drug such that the robotic device can be used for drug delivery. In another example, the body may include a sensor such that the robotic device can be used for sensing or monitoring applications, e.g., in vivo or in vitro. The rigid body parts of the body may be movably connected with each other through any types of joints. The structure forming the joints, e.g., the pivot-type joints, may be constructed and shaped differently. The body parts can be detachably connected in some cases. The rigid body parts may have structures equivalent to the arm portions for motion transmission. The arm portions can be of any shape and size. The magnetic responsive material may be applied to different parts of the body, although preferably at or near the end(s) of the device to maximize the moment created by magnetic interaction. The robotic device is preferably a micro-robot in the scale of microns.

For example, the method of making a robotic device can be different from that illustrated. The body can be formed using technologies other than 3D printing and laser lithography. The magnetic responsive material may be applied to the body using methods such as but not limited to electron beam deposition, dipping, electroplating, sputtering, or chemical vapor deposition. In some cases, the magnetic responsive material may be embedded in the body or the body part. In some applications, the shielding of the remainder of the body parts is not necessary during application of the magnetically responsive material. The materials used to make the body can also vary so long as the rigidity of the body is preserved.

For example, the magnetic control system may be modified for different control applications. The number of magnets used can be any number larger than or equal to two, distributed differently. The magnets can be permanent magnets, electromagnets, or the like. The magnets may be supported by a frame, a platform, a housing, or the like. The shape and form of the frame, platform, or housing can be different. The frame, platform, or housing can be motorized or otherwise driven to move, preferably rotate, and more preferably oscillate about an axis. Movement of the frame, platform, or housing is preferably controllable to affect movement of the magnetically controlled robotic device. Different changing magnetic fields can be applied by the magnets. For example, the changing magnetic field may be an oscillating or a non-oscillating magnetic field. The changing magnetic field may be changed uniformly or non-uniformly, dependent on applications.

The invention claimed is:

1. A magnetically-controllable robotic device, comprising:
   a body having
     a first rigid body part that generally elongates along and is symmetric about a first long axis, the first rigid body part comprising a first arm portion and a second arm portion, and
     a second rigid body part movably connected with the first rigid body part;
   wherein the first arm portion and the second arm portion are arranged symmetrically about the first long axis for interacting with the second rigid body part,
   wherein the first rigid body part is pivotable relative to the second rigid body part between a first end position, in which the first arm portion contacts one side of the second rigid body part, and a second end position, in which the second arm portion contacts an opposite side of the second rigid body part; and
   wherein the first rigid body part is magnetically-responsive such that the first rigid body part can be controlled by an external magnetic field generated by an magnetic control system.

2. The magnetically-controllable robotic device of claim 1, wherein the second rigid body part is movably connected with the first rigid body part through a joint.

3. The magnetically-controllable robotic device of claim 2, wherein the joint is a pivot-type joint through which the second rigid body part pivotably connects with the first rigid body part.

4. The magnetically-controllable robotic device of claim 3, wherein the pivot-type joint is provided partly by the first rigid body part and partly by the second rigid body part.

5. The magnetically-controllable robotic device of claim 4, wherein the first rigid body part comprises a first connection portion and the second rigid body part comprises a second connection portion connected with the first connection portion, and wherein the first connection portion and the second connection portion provide the pivot-type joint.

6. The magnetically-controllable robotic device of claim 5, wherein the first connection portion and the second connection portion are non-detachably connected with each other.

7. The magnetically-controllable robotic device of claim 6, wherein one of the first connection portion and the second connection portion comprises a rod, and the other of the first connection portion and the second connection portion defines an opening through which the rod extends.

8. The magnetically-controllable robotic device of claim 7, wherein the rod and the opening are correspondingly shaped and sized such that a clearance exists between the rod and the opening.

9. The magnetically-controllable robotic device of claim 1, wherein the second rigid body part generally elongates along a second long axis, and the second rigid body part is symmetric about the second long axis.

10. The magnetically-controllable robotic device of claim 9, wherein the first long axis and the second long axis are collinear.

11. The magnetically-controllable robotic device of claim 1, wherein the first rigid body part comprises a U-shaped portion that is formed at least partly by the first arm portion and the second arm portion.

12. The magnetically-controllable robotic device of claim 5, wherein the body further comprises a third rigid body part pivotably connected with the second rigid body part through a further pivot-type joint.

13. The magnetically-controllable robotic device of claim 12, wherein the second rigid body part comprises a further second connection portion and the third rigid body part comprises a third connection portion connected with the further second connection portion, wherein the first connection portion and the second connection portion provide the further pivot-type joint.

14. The magnetically-controllable robotic device of claim 13, wherein one of the further second connection portion and the third connection portion comprises a rod, and the other of the further second connection portion and the third connection portion defines an opening through which the rod extends.

15. The magnetically-controllable robotic device of claim 13, wherein the second connection portion and the further second connection portion are arranged at opposite ends of the second rigid body part.

16. The magnetically-controllable robotic device of claim 15, wherein one of the second connection portion and the further second connection portion comprises a rod, and the other of the second connection portion and the further second connection portion defines an opening for receiving a rod.

17. The magnetically-controllable robotic device of claim 1, wherein the magnetically-controllable robotic device further comprises magnetically-responsive material arranged on at least part of a surface of the first rigid body part that makes the first rigid body part magnetically-responsive.

18. The magnetically-controllable robotic device of claim 17, wherein the magnetically-responsive material is in the form of a coating arranged on at least part of the first rigid body part.

19. The magnetically-controllable robotic device of claim 18, wherein the magnetically-responsive coating is arranged on only part of the first rigid body part and other parts of the magnetically-controllable robotic device are devoid of magnetically-responsive material.

20. The magnetically-controllable robotic device of claim 17, wherein the magnetically-responsive material contains metallic material, and wherein the metallic material comprises: nickel, iron, cobalt, neodymium, or any of their combination.

21. The magnetically-controllable robotic device of claim 1, wherein the first rigid body part and the second rigid body part are integrally formed using a photo-curable material.

22. The magnetically-controllable robotic device of claim 1, wherein the magnetically-controllable robotic device is tetherless.

23. A method for making a magnetically-controllable robotic device, comprising:
    forming a body, the body having
        a first rigid body part that generally elongates along and is symmetric about a first long axis and comprising a first arm portion and a second arm portion, and
        a second rigid body part movably connected with the first rigid body part,
        the first arm portion and the second arm portion being arranged symmetrically about the first long axis for interacting with the second rigid body part, and
        the first rigid body part being pivotable relative to the second rigid body part between a first end position, in which the first arm portion contacts one side of the second rigid body part, and a second end position, in which the second arm portion contacts an opposite side of the second rigid body part; and
    arranging the first rigid body part to be magnetically-responsive such that the first rigid body part can be controlled by an external magnetic field generated by an magnetic control system.

24. The method of claim 23, wherein arranging the first rigid body part to be magnetically-responsive comprises applying magnetically-responsive material on at least part of a surface of the first rigid body part.

25. The method of claim 24, wherein the application of magnetically-responsive material on at least part of a surface of the first rigid body part is performed using electron beam deposition, dipping, electroplating, sputtering, or chemical vapor deposition.

26. The method of claim 24, wherein the magnetically-responsive material is arranged in the form of a magnetically-responsive coating on at least part of a surface of the first rigid body part.

27. The method of claim 26, wherein the magnetically-responsive coating is arranged on only part of a surface of the first rigid body part.

28. The method of claim 24, further comprising shielding other parts of the body when magnetically-responsive material or coating is applied on at least part of the surface of the first rigid body part.

29. The method of claim 24, wherein the magnetically-responsive material contains metallic material, wherein the metallic material comprises: nickel, iron, cobalt, neodymium, or any of their combination.

30. The method of claim 23, wherein forming the body comprises integrally forming the body with the first rigid body part and the second rigid body part such that the first rigid body part and the second rigid body part are not detachable.

31. The method of claim 23, wherein forming the body comprises performing laser lithography on a photo-curable material to form the body.

32. The method of claim 31, wherein the photo-curable material comprises: polymer, ceramics, nanofiber, or any of their combination.

* * * * *